United States Patent
Schneider et al.

(10) Patent No.: US 7,000,454 B2
(45) Date of Patent: Feb. 21, 2006

(54) PARTICLE MEASUREMENT CONFIGURATION AND SEMICONDUCTOR WAFER PROCESSING DEVICE WITH SUCH A CONFIGURATION

(75) Inventors: Claus Schneider, Bubenreuth (DE); Ralph Trunk, Bischberg (DE); Lothar Pfitzner, Erlangen (DE); Heinz Schmid, Erlangen (DE)

(73) Assignees: Infineon Technologies AG, Munich (DE); Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 544 days.

(21) Appl. No.: 10/233,878

(22) Filed: Sep. 3, 2002

(65) Prior Publication Data

US 2003/0041969 A1    Mar. 6, 2003

(30) Foreign Application Priority Data

Sep. 3, 2001    (DE) ................................ 101 43 075

(51) Int. Cl.
*G01N 19/00* (2006.01)

(52) U.S. Cl. .................................... 73/31.03

(58) Field of Classification Search .............. 73/31.02, 73/31.07, 61.41; 156/345.15; 118/665, 118/688, 689
See application file for complete search history.

(56) References Cited

U.S. PATENT DOCUMENTS

| | | | | |
|---|---|---|---|---|
| 5,138,869 A | * | 8/1992 | Tom | 73/31.03 |
| 5,583,282 A | * | 12/1996 | Tom | 73/31.03 |
| 5,810,928 A | * | 9/1998 | Harada et al. | 118/690 |
| 6,044,689 A | * | 4/2000 | Yoshida et al. | 73/31.03 |
| 6,172,376 B1 | * | 1/2001 | Xu et al. | 250/574 |
| 6,205,842 B1 | * | 3/2001 | Patashnick et al. | 73/28.01 |
| 6,314,986 B1 | * | 11/2001 | Zheng et al. | 137/240 |
| 6,386,015 B1 | * | 5/2002 | Rader et al. | 73/31.05 |
| 2002/0096211 A1 | * | 7/2002 | Zheng et al. | 137/240 |
| 2003/0041969 A1 | * | 3/2003 | Schneider et al. | 156/345.15 |
| 2003/0197852 A1 | * | 10/2003 | Johnson et al. | 356/37 |
| 2004/0159399 A1 | * | 8/2004 | Misra et al. | 156/345.15 |

FOREIGN PATENT DOCUMENTS

| | | |
|---|---|---|
| GB | 2 295 232 A | 5/1996 |
| JP | 05306988 A | 11/1993 |
| JP | 07198556 A | 8/1995 |

* cited by examiner

*Primary Examiner*—Hezron Williams
*Assistant Examiner*—John Fitzgerald
(74) *Attorney, Agent, or Firm*—Laurence A. Greenberg; Werner H. Stemer; Ralph E. Locher

(57) ABSTRACT

A particle measurement configuration measures the particle concentration in a liquid or gaseous medium by way of a particle measuring instrument. In order to avoid erroneous measurements or damage to the particle measuring instrument, a measuring cell is provided which measures temperature or pressure or pH of the medium. A system controller shuts off a valve if threshold values are exceeded and it prevents the particle measuring instrument from being operated outside a predefined specification.

15 Claims, 3 Drawing Sheets

PARTICLE MEASUREMENT CONFIGURATION AND SEMICONDUCTOR WAFER PROCESSING DEVICE WITH SUCH A CONFIGURATION

BACKGROUND OF THE INVENTION

1. Field of the Invention

The invention relates to a particle detector measuring instrument with a feed connection for a gaseous or liquid medium, and a measuring instrument for measuring the concentration of particles in the medium. The invention additionally relates to a device for processing semiconductor wafers which comprises such a particle measuring configuration, in order to control the processing on the basis of a signal generated by the measuring configuration.

During the production of particle-sensitive products, the contamination monitoring of the gas or liquid media processed assumes great importance. In particular during the production of electronic components on semiconductor wafers, because of the progressive automation and the structure widths becoming smaller and smaller, there is an increasing need for the most comprehensive contamination monitoring possible.

Particle measuring instruments are known which measure the concentration of particles within the gas or liquid medium. It is possible for solid-body particles or liquid particles in gases or solid-body particles in liquids to be detected. If, within a processing device for semiconductor production, the particle concentration has to be determined during operation (in situ), the measuring instrument is incorporated into a circulating or disposing medium flow. The particle measuring instrument is controlled via communication lines, and measured data values that are determined are interrogated. The instruments are constructed for use only within a specified range of fluctuation of operating conditions. If these operating conditions are exceeded, then there is a risk that erroneous measurements will be output, imparting a false image of the real relationships; in the limiting case, the particle measuring instrument can even be destroyed.

For example, in the area of deposition ovens for the thermal growth of layers, when the oven is being unloaded hot air can reach a particle sensor monitoring the mini environment, in such a way that the sensor is destroyed. In the area of wet-chemical processing with acids and alkalis, a pH of the liquid medium can rise in aggressive areas to such an extent that a sensor is likewise destroyed. In addition, the operating parameters of the medium can reach peak values within which the measuring sensor no longer operates reliably. In order to achieve permanent and automatic process monitoring, such conventional particle sensors are not reliable enough and are therefore unsuitable.

SUMMARY OF THE INVENTION

It is accordingly an object of the invention to provide a particle measuring instrument configuration, which overcomes the above-mentioned disadvantages of the heretofore-known devices and methods of this general type and which is improved so that the system recognizes operation of the particle measuring instrument contained in the configuration outside predefined specifications of the media to be measured, in order to avoid erroneous measurements or even destruction of the particle measuring instrument per se. It is a further object to specify a device for processing semiconductor wafers which permits reliable operation while using such an configuration of particle measuring instruments.

With the foregoing and other objects in view there is provided, in accordance with the invention, a particle measurement configuration, comprising:
- a feed connection for gaseous or liquid medium (fluidic medium);
- a first measuring instrument for measuring a concentration of particles in the medium;
- a second measuring instrument for measuring a parameter different from the concentration of particles in the medium;
- a valve connected in series with the feed connection, the first measuring instrument, and the second measuring instrument; and
- a control unit operatively connected to the valve, the control unit being coupled to the second measuring instrument for receiving a signal representing the parameter, the control unit comparing the signal with a predefined threshold value and controlling a switching state of the valve based on the comparison.

In other words, the configuration of particle measuring instruments according to the invention comprises: a feed connection for a gaseous or a liquid medium; a first measuring instrument for measuring the concentration of particles in the medium; a second measuring instrument for measuring a parameter different from the aforementioned concentration of the medium; a first valve, which is connected in series with the feed connection, the first measuring instrument and the second measuring instrument; and a control unit, which is coupled to the second measuring instrument in order to receive a signal representing the parameter and compare the signal with a predefined threshold value, and in order to control the switching state of the first valve on the basis of this comparison.

In addition to the first measuring instrument for measuring the contamination of the medium by solid-body or liquid particles, the actual particle measuring instrument, the configuration of particle measuring instruments has a further, second measuring instrument which is used to measure a different parameter of the gaseous or liquid medium to be examined. The measured value obtained for the parameter is compared with a threshold value or a permissible value range in a control unit. If the measured value lies outside the desired permissible specification, then the valve connected in series with the actual particle counter in the medium flow is shut off. The medium flow which has characteristics lying outside the specification is kept away from the actual particle measuring instrument, in order to avoid destruction of the sensor or an erroneous measurement.

The second, additional measuring instrument is, for example, a measuring cell or a measuring sensor which is introduced into the flow of the medium to be monitored and continuously measures the parameter to be monitored. Both in the case of liquid and in the case of gaseous media, the temperature, the pressure or the pH of the medium can be measured as a significant parameter. For this purpose, appropriate measuring cells including suitable measuring sensors and the appropriate signal evaluation are readily known per se from the prior art. In the case of gaseous media, the temperature generally plays the major role. In the case of liquid media, temperature, pressure or pH can be of significance.

If, because the specification has been exceeded, the gas flow is turned off by shutting off the valve, then no current medium is supplied to the measuring cell any more, so that a return to permissible specifications for the measured parameter is no longer detected. In order to reset the configuration, therefore, the control unit is provided with an input terminal in order to reset and to open the valve again. Such a control signal is expediently supplied by the higher-order control unit of the process device into which the configuration of particle measuring instruments has been integrated. With regard to the sequence of valve, particle measuring instrument per se and measuring cell or measuring sensor, various advantageous refining variants are conceivable. In the flow direction of the medium supplied, the valve can be positioned upstream or downstream of the measuring cell and upstream or downstream of the particle measuring instrument. If, for example, the measuring sensors used change the particle distribution or particle size distribution itself by emitting particles, then it is beneficial to install these measuring sensors downstream of the particle measuring instrument in the flow direction, that is to say entirely at the end of the series circuit. If the thermal conductivity of the medium is very high, it is beneficial to position the valve upstream of the particle measuring instrument and downstream of the measuring sensor. The valve can even be arranged upstream of the measuring cell. Destruction of the particle measuring instrument or measuring cell in a quiescent medium is then prevented. During actuation, the valve can itself produce particles with its moving parts. These particles can influence the particle distribution in the medium flow. When the valve is opened, the particles produced in this way can lead to a short-term change in the particle size distribution. In order to take this effect into account when measurements are resumed, a dead time of the measurement of the particle contamination or particle concentration in the medium by the particle measuring instrument is dictated after the valve has been opened.

If the medium is sucked through the measuring cell and particle measuring instrument by means of a pump, it is expedient to provide a second valve in order to prevent a negative pressure in the measuring chamber both of the particle measuring instrument and of the measuring cell. The second valve is therefore connected down-stream of the particle measuring instrument and upstream of the pump. This avoids the particle concentration to be measured being affected by the suction operation of the pump. The two valves are expediently controlled in the same direction by the control unit.

The measured variables such as temperature, pressure or pH change differently in a quiescent medium than in a flowing medium. The further flow is expediently ensured by a bypass. For this purpose, the first and second valves are designed as changeover valves, so that the flow through the particle measuring instrument is stopped and led past it in parallel.

Finally, in relation to one or both of the valves described, it is advantageous additionally to provide a further changeover valve, through which a flushing medium, for example deionized water, can be supplied. The deionized water is supplied to the medium flow through the valve connected upstream in the flow direction, and it is carried away again through the second valve connected downstream. Both of the additional changeover valves serving to supply and remove flushing agent are arranged directly on the side of the particle measuring instrument and connected downstream of the first changeover valve and upstream of the second changeover valve.

As explained above, the configuration of particle measuring instruments according to the invention is suitable in particular for use in a device which is suitable for processing semiconductor wafers. Such semiconductor wafers are subjected to a large number of processing steps such as layer deposition, structuring, etching, cleaning, etc., in order to produce integrated semiconductor circuits, computer hard disks, storage media such as CD ROMs, flat monitors or masks for the exposure of semiconductor wafers. During the processing, the signal generated by the particle measuring instrument is used for process control. In the simplest case, when a predefined threshold value of particle concentration is exceeded, a warning signal is generated in order to interrupt the processing of the semiconductor wafers, and then to initiate suitable measures for eliminating the exceeding of the threshold value.

One application in the area of liquid aggressive media, such as acids or alkalis, lies in a spray processor. The latter comprises a flushing chamber in which the liquid removed from the tank is monitored for the particle concentration, in order on this basis, for example, to define a time for renewal of the flushing medium. For example, the temperature of the liquid removed and sucked through the particle measuring instrument can fluctuate. If the specification range of the measuring instrument is exceeded, the measurement is switched off. Further applications in the liquid area are wet benches for wet-etching or cleaning semi-conductor wafers. The configuration of particle measuring instruments according to the invention can be used both in disposal lines and in circulation systems where liquid is always removed and examined by the particle measuring instrument and then transported back into the tank again through a pump and a filter.

Another application in the gaseous area consists, for example, in monitoring the particle concentration in a closed clean room of a semiconductor fabrication device, a mini environment, as it is known. For example, particles are produced there when handling devices are maladjusted and produce particles to a greater extent as a result of abrasion, or if transport boats for semiconductor wafers are loaded by parasitic deposition to such an extent that particles and layers separate. The increased particle concentration is determined in the internal air sucked away out of the mini environment. The problem in this case is that, in particular in high-temperature processes in ovens for the thermal growth of layers, the temperature immediately after the removal of a wafer boat from the oven briefly rises very sharply. The sensitive particle measuring instrument could be destroyed by the hot air sucked past the measuring instrument by a pump. The measuring cell connected upstream determines the temperature increase and shuts the valve off, so that for a short time the hot air is kept away from the particle measuring instrument.

Other features which are considered as characteristic for the invention are set forth in the appended claims.

Although the invention is illustrated and described herein as embodied in a configuration of particle measuring instruments and a semiconductor wafer processing device having such an configuration, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
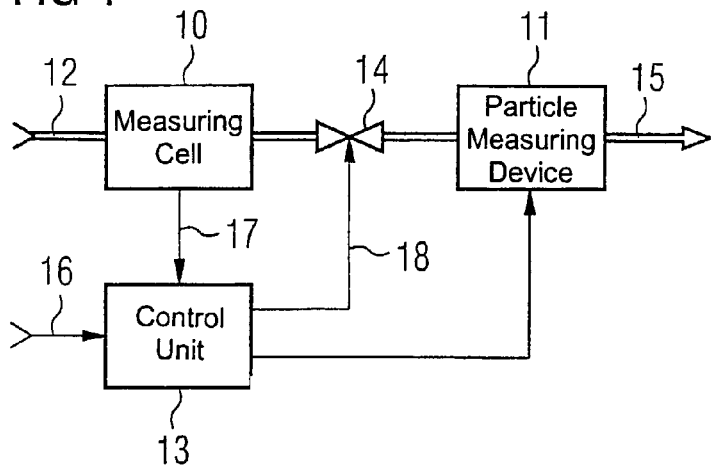
FIG. 1 is a basic block circuit diagram of a configuration of particle measuring instruments according to the invention.

Referring now to the figures of the drawing in detail and first, particularly, to FIG. 1 thereof, there is shown a conventional particle measuring instrument 11 which is known per se. It is available as standard and it is used to determine the contamination with microscopic solid-body particles of a gaseous or liquid medium flow supplied at a connection 12. The medium flow is discharged at the output connection 15 and disposed of or supplied to a return circuit. Connected upstream of the particle measuring instrument is a measuring cell 10 which measures a further parameter, that is to say not the particle concentration. The measuring cell is, for example, a temperature sensor, a pressure sensor or, in the case of liquid and gaseous aggressive media, a pH sensor which is kept in the medium flow in order there to measure the appropriate characteristic of the medium flowing past. A signal representing the temperature, the pressure or the pH is supplied via a communications line 17 to a control unit 13, for example an evaluation computer. The evaluation program in the control unit 13 has a threshold value or a specification window preset. If the threshold value or the limits of the specification window are exceeded, this indicates that permissible operating conditions are exceeded, so that the particle measuring instrument 11 is being charged with medium outside its allowable specification range. At a terminal 18, the control unit 13 generates an actuating signal which shuts off a valve 14 arranged between measuring cell 10 and particle measuring instrument 11. The particle measuring instrument 11 is thus separated from the medium flow lying outside the specification. Erroneous measured values or even destruction of the particle measuring instrument 11 are avoided.

Figure 6:
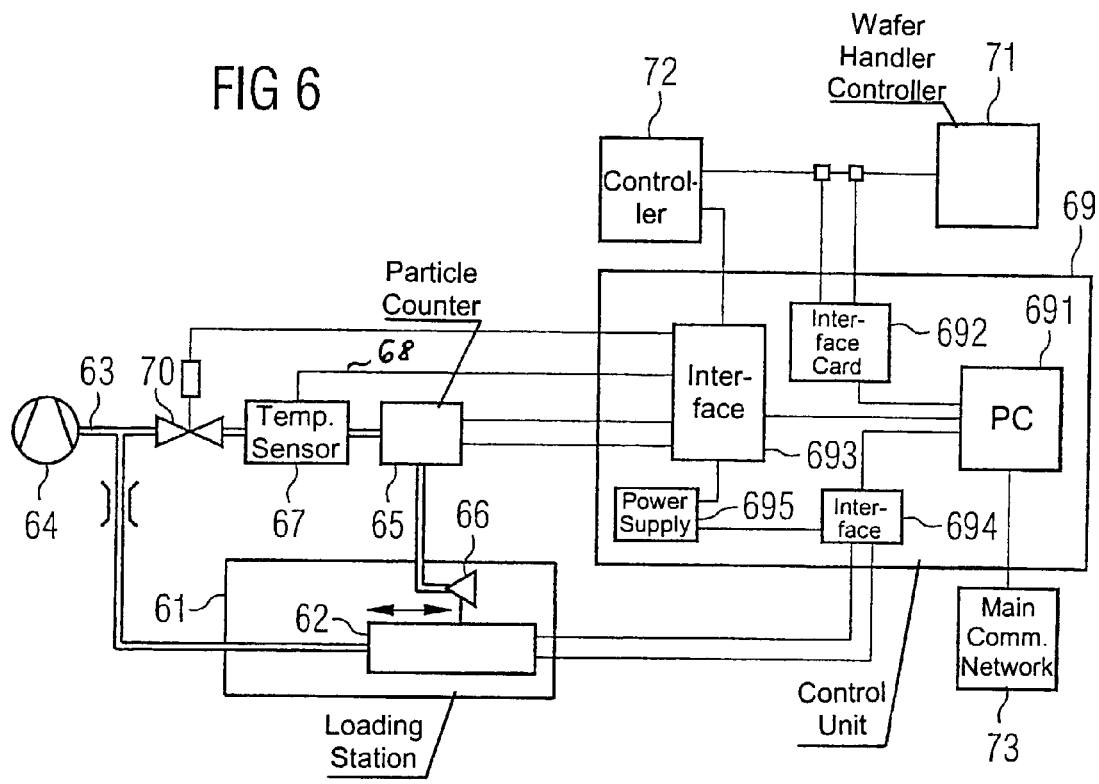
FIG. 6 shows an exemplary embodiment of monitoring a gaseous medium in the loading area of a high-temperature oven for the thermal coating of semiconductor wafers.

For example, the configuration of measuring instruments is provided to monitor a mini environment of the loading station of a high-temperature oven for semi-conductor wafers, see FIG. 6. A wafer boat processed in the oven is just being removed and moved into the loading area. Very hot air is sucked into the connection 12 and threatens to destroy the particle measuring instrument 11. The sharply elevated temperature is determined by the measuring cell 10 with the aid of a temperature sensor and is compared with the threshold value programmed in the control unit 13. The valve 14 is shut off immediately in order to avoid the destruction of the particle measuring instrument. When the temperature of the air in the loading area of the oven has fallen to such an extent that normal operating conditions are present, the process device notifies the control unit 13 via the signal line 16. In turn, the control unit 13 opens the valve 14.

Within the series circuit of measuring cell 10, valve 14 and particle measuring instrument 11, various sequences of the configuration are conceivable. The measuring cell can thus be connected downstream of the particle measuring instrument. The valve is preferably connected upstream of the particle measuring instrument, but can also be connected downstream of the particle measuring instrument. Finally, the particle measuring instrument can be arranged first in the medium flow, followed by the measuring cell, and finally the shut-off valve. In all cases, the media supplied to the particle measuring instrument are monitored by suitable sensors arranged in the measuring cell. If the defined specification windows of the parameters to be monitored are left, the flow of the medium through the particle measuring instrument is interrupted by shutting off the valve. If the measuring cell should change the particle size distribution, then, as described previously, it should expediently be arranged downstream of the particle sensor in the flow direction. If the thermal conductivity of the medium is high, the shut-off valve should preferably be positioned upstream of the particle measuring instrument. If a switch-on command is communicated via the signal line 16 again, the control unit 13 arranges for the particle counter to wait for a dead time before the start of a new measurement, in order to ensure that particles produced by the operation of switching the valve 14 on pass through the particle measuring instrument 11 first without falsifying a measurement.

Figure 2:
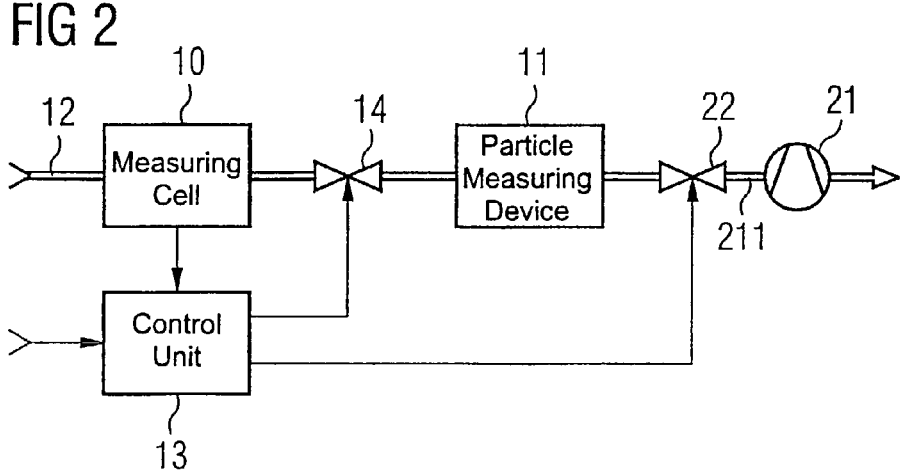
FIG. 2 shows a configuration having two valves.

The medium can be transported through the particle measuring instrument by means of pressure present on the connection 12 or aspirated in by means of a pump 21 connected downstream. The latter option is illustrated in FIG. 2. In order to avoid the particle measuring instrument 11 being destroyed by the negative pressure produced by the pump 21 when the valve 14 is shut off, a further valve 22 is connected upstream of the pump 21 and downstream of the particle measuring instrument. The valves 14, 22 are controlled in the same direction by the control unit 13, that is to say both are shut off at the same time or turned on at the same time. Here, too, all the configurations relating to the sequence of particle measuring instrument and measuring cell are conceivable. In any case, the valve 14 should be connected upstream of the particle measuring instrument 11, and the valve 22 should be connected downstream.

Figure 3:
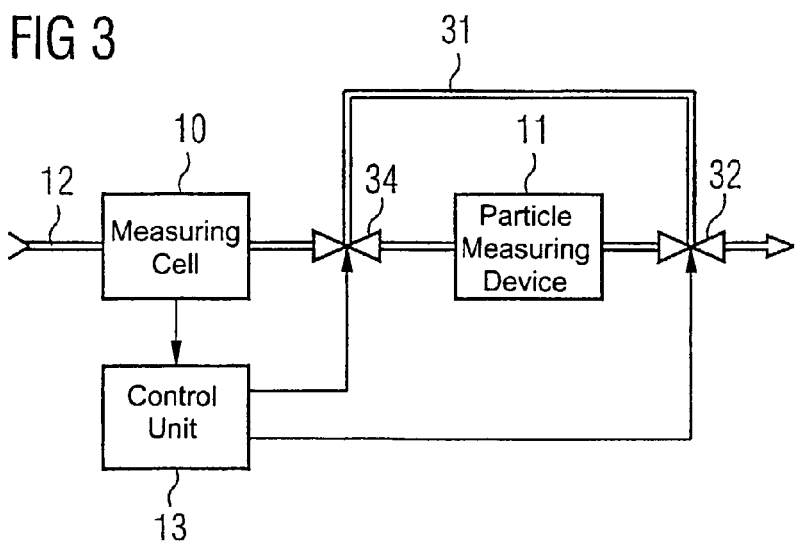
FIG. 3 shows a configuration having two changeover valves and a bypass bypassing the particle measuring instrument.

In order to maintain the flow through the measuring cell 10 even when the medium flow is blocked by the particle measuring instrument 11, in FIG. 3 an additional line 31 is provided which, in this case, bypasses the measuring instrument 11. The valves 34 and 32 connected upstream and downstream of the particle measuring instrument 11 are now designed as changeover valves. In each case one of the connections of the changeover valves 34, 32 is connected to the bypass 31. The valves 34, 32 are driven by the control unit 13 in such a way that, in the event of the specification being exceeded, as determined by the measuring cell 10, the flow is separated from the particle measuring instrument 11 and led past the measuring instrument via the bypass 31 led in parallel thereto.

Figure 4:
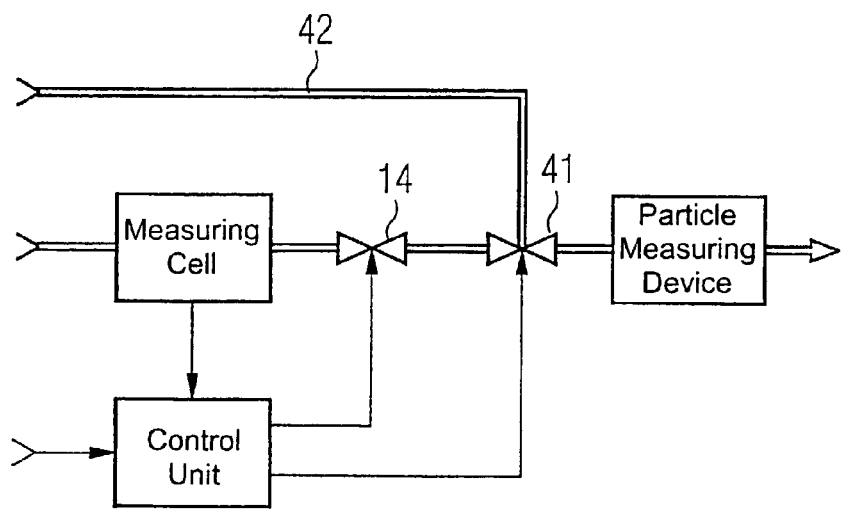
FIG. 4 shows an embodiment of the configuration having a flushing valve.
Figure 5:
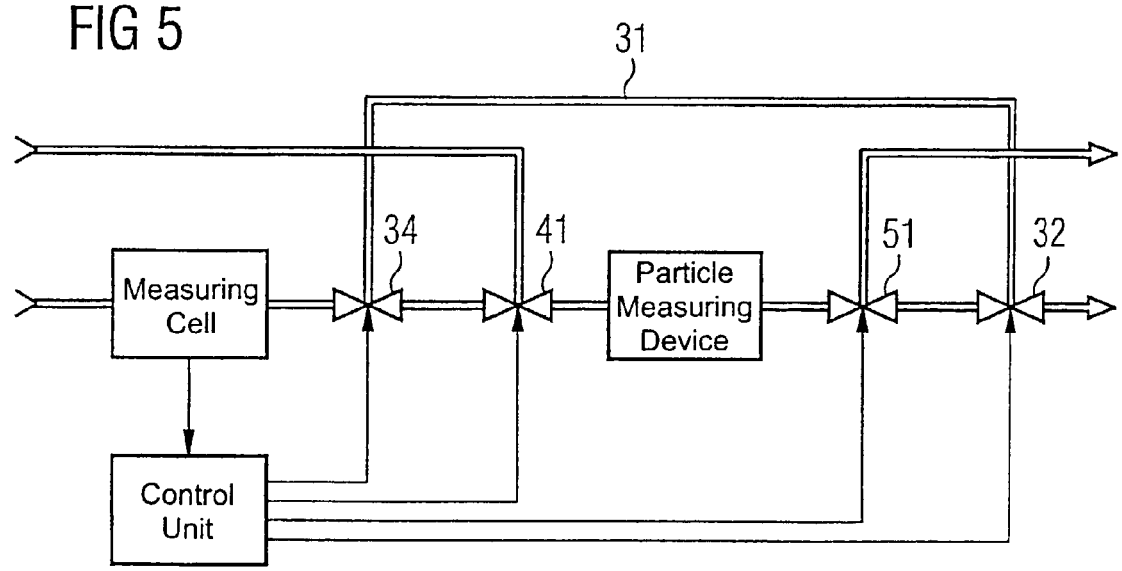
FIG. 5 shows a configuration having two flushing valves including a bypass.

FIG. 4 shows that a changeover valve 41, via which a flushing medium can be supplied to a connection 42, is connected downstream of the valve 14. As a result, the particle measuring instrument 11 is kept free of contaminants. The flushing medium used is, for example, deionized water. Finally, FIG. 5 shows the variant with a bypass, in which, firstly, the valve 41 for supplying the flushing medium is connected immediately downstream of the first changeover valve 34 and, secondly, a changeover valve 51 is connected upstream of the downstream changeover valve 32, in order to carry the flushing medium supplied away again. The particle measuring instrument can be cleaned with flushing medium when the bypass line 31 is activated.

A basic circuit diagram of a high-temperature oven is shown in FIG. 6. In a thermal process, which runs at a temperature up to 1000° C. or more, for example, layers are deposited on the semiconductor wafers. The semiconductor wafers are supplied to the high-temperature oven in a wafer boat as an entire batch. In order to load and unload batches to be processed or already processed in wafer boats, use is made in the loading station 61 of a handling device for wafers (wafer handler). The wafer handler is operated with a negative pressure in order to fix wafers by suction. Arranged on a movement rail 62 is a movable probe 66, in order to extract particles which are produced by movement and handling operations. The movement rail is supplied from a negative-pressure or vacuum line 63 present everywhere in the fabrication line. A vacuum pump 64 supplies the negative-pressure line 63 with vacuum. The particle concentration in the inner environment of the loading area 61 is increased, for example, when the handling device 62 for loading and unloading the wafer boats is maladjusted. The particles are produced by increased abrasion and impact effects. Another source of an increased particle concentration is the wafer boat itself. In this environment, wafer boats are composed of quartz glass which, in the high-temperature oven, is likewise coated parasitically with material. Above a certain layer thickness, there is increasingly a risk that the parasitically deposited layer will fracture and split off and possibly effect impermissible contamination in the oven, so that the yield of serviceable integrated circuits decreases. The rupturing of the parasitic layer on the wafer boat produces particles, which are likewise detected by the particle counter 65. The particle counter is likewise supplied with vacuum by the pump 64 and the suction line 63. It aspirates in the ambient air in the mini environment, for example via a suction opening 66 connected to the wafer handler 62.

When a wafer boat is removed from the oven, it can have a temperature of the order of magnitude of 600° Celsius. Relatively hot air can therefore get to the particle counter 65 for a short time, so that the measurement would be disrupted or even the particle counter itself could be destroyed. A temperature sensor 67 connected downstream of the particle counter 65 in the suction direction determines the temperature of the air taken in and communicates this via a line 68 to a control unit 69. The control unit 69 has, for example, a personal computer 691, an interface card 692, an interface device 693 which drives the particle counter 65, the temperature sensor 67 and a valve 70 through analog and digital channels and receives control signals. Finally, the control unit 69 contains an interface 694 for driving the movement rail 62 and also a power supply unit 695. The control unit 69 is connected via respective communications links to a controller 72 for the high-temperature oven and the wafer handler controller 71. Finally, the control unit 69 is incorporated into the communications network of the entire semiconductor factory 73. If the personal computer 691 detects that the temperature sensor 67 uses the interface 693 to communicate the fact that the air sucked in via the suction opening 66 and the particle counter 65 exceeds the preset thres-hold value, then the interface 693 generates an actuating signal in order to shut the valve 70 off. The air stream sucked through the particle counter 65 is stopped, and longer-term exceeding of the temperature of the air loading the particle counter 65 is avoided. After a certain temperature of the cooling boat has been reached which is measured by the oven controller 72, the air in the loading station 61 is also within the specifications of the particle counter 65 again. In response to a signal from the oven controller 72 to the control unit 69, the valve 70 is released by the control unit 69 again. The particle counter can then monitor the mini environment for an impermissibly high concentration and indicate maladjustment of the wafer handler or the end of the operating time for a sufficiently used wafer boat.

Figure 7:
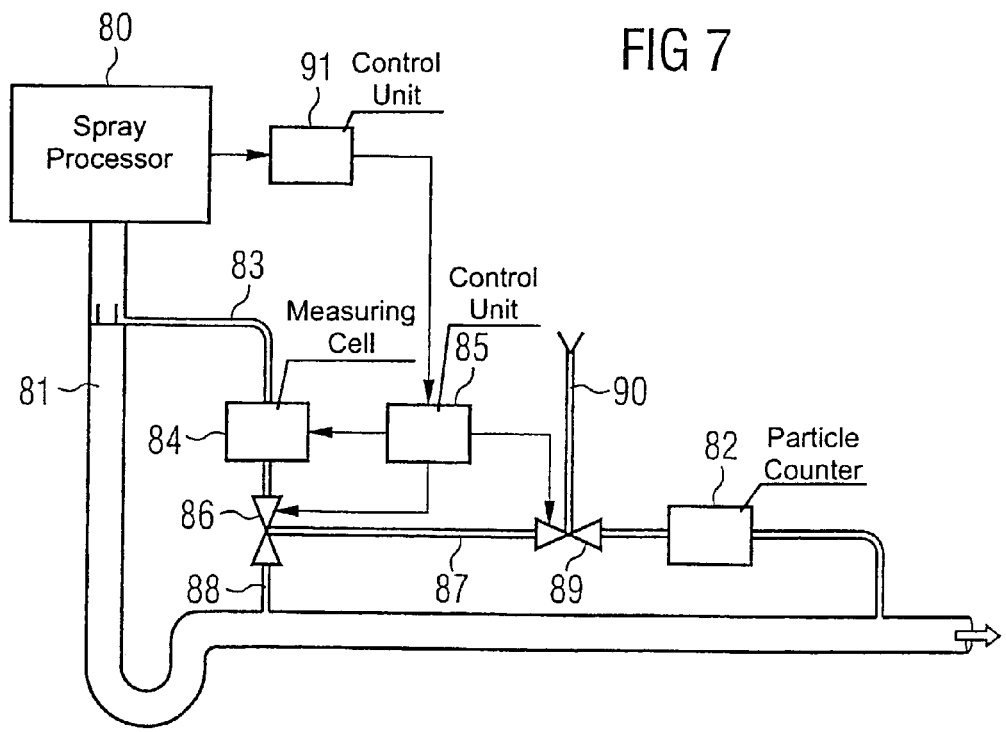
FIG. 7 illustrates an exemplary embodiment of monitoring liquid media in the sequence of a wet-cleaning device for semiconductor wafers.

Another application of the configuration of particle measuring instruments according to the invention for liquid media to be monitored is illustrated in FIG. 7. A spray processor 80, as it is known, is used to clean semiconductor wafers. A wafer cassette rotates within a drum having spray valves which are arranged centrally and circumferentially. The drum sprays acid or alkali onto the wafers to be cleaned. The liquid flowing away is carried in a line 81 to neutralization. In a side channel 83, a particle counter 82 is supplied with part of the medium led away to neutralization. The particle counter 82 provides, for example, a signal to terminate the cleaning operation. The problem is that the pH of the flushing medium or its temperature can fluctuate. A measuring cell 84, which is connected upstream of the particle counter 82 and supplied with the liquid to be monitored by the line 83, determines temperature and/or pH. If the specification limits are exceeded, a control unit 85 switches on a changeover valve 86, which shuts off the branch 87 which leads to the particle counter 82, and feeds the medium supplied via the connection 83 into the neutralization channel 81 again via the line 88. Connected upstream of the particle counter 82 is a further changeover valve 89, which is supplied at the connection 90 with deionized water in order to flush the particle counter 82 even when the line 87 is shut off, in order in this way to prevent deposits as a result of drying out. The changeover valve 89 is activated by the control unit 85. Since, in such spray processors 80, liquid is not always discharged into the neutralization channel 81, the particle counter 82 can run dry even when there is an admissible temperature or admissible pH. In order to prevent this, the valve 89 is controlled, by the control unit 91 coupled to the spray processor 80 and the control unit 85, in such a way that a flushing medium is led through the particle counter 82 via the line 90 and the valve 89.

Configurations of particle measuring instruments with an additional measuring cell and shut-off valves in the embodiments described above can also be used at many other points. Ideally, they are suitable for monitoring the contamination in closed-off clean-room-like mini environments in semiconductor fabrication. Of course, the invention can also advantageously be used in all other production technologies which use clean rooms. The invention is suitable for monitoring both gaseous and liquid media. The latter applications may be wet-chemical plants for etching or cleaning semiconductor wafers. The configuration according to the invention can be used both in disposal lines and in circulation systems.

We claim:

1. A particle measurement configuration, comprising:
   a feed connection for gaseous or liquid medium;
   a first measuring instrument for measuring a concentration of particles in the medium;
   a second measuring instrument for measuring a parameter different from the concentration of particles in the medium;

a first valve connected in series with said feed connection, said first measuring instrument, and said second measuring instrument, said first valve being connected upstream of said first measuring instrument in a flow direction of the medium;

a control unit operatively connected to said first valve, said control unit being coupled to said second measuring instrument for receiving a signal representing the parameter, said control unit comparing said signal with a predefined threshold value and controlling a switching state of said first valve based on the comparison;

a pump having a suction connection connected downstream of said first and second measuring instruments and said first valve; and a second valve connected downstream of said first measuring instrument.

2. The configuration according to claim 1, wherein said second measuring instrument is configured to measure a parameter selected from the group consisting of a temperature, a pressure, and a pH of the medium.

3. The configuration according to claim 1, wherein said control unit is coupled to said first and second valves and configured to control switching states of said valves in the same direction.

4. The configuration according to claim 1, wherein said first and second valves are changeover valves, and further comprising a line parallel to said first measuring instrument and connected between said changeover valves.

5. The configuration according to claim 1, wherein said control unit has an input terminal for receiving a control signal, and said control unit is configured to open said first valve based on the control signal.

6. The configuration according to claim 5, wherein said control unit is coupled to said first measuring instrument for suppressing a measurement of the concentration of particles in the medium for a predefined time period after the first valve has been opened.

7. The configuration according to claim 1, wherein said first and second valves are changeover valves and a third changeover valve is connected downstream of said first valve, is coupled to a connection for a flushing medium, and is coupled to said control unit, to supply a flushing agent to the series circuit via said third valve when said first valve is shut off.

8. The configuration according to claim 7, which further comprises a fourth valve connected downstream of said second valve and coupled to said control unit, wherein, when the flushing medium is supplied into the series circuit, the flushing medium is supplied away from the series circuit via said fourth valve.

9. A device for processing semiconductor wafers, comprising a process controller for controlling a processing of the semiconductor wafers, and a particle measurement configuration according to claim 1 configured to output a signal with the first measuring instrument, and wherein said process controller controls the processing of the semiconductor wafers based on the signal representing a particle concentration in the medium.

10. The device according to claim 9, which comprises a cleaning configuration for cleaning the semiconductor wafers with an aggressive liquid, said feed connection of the particle measurement configuration communicating with said cleaning configuration.

11. The device according to claim 10, wherein the aggressive liquid is an acid or a base.

12. The device according to claim 9, which comprises a high-temperature oven for the thermal growth of layers on the semiconductor wafers, and a loading station coupled to said oven, wherein said loading station encloses an inner, cleaned environment, and said feed connection is coupled to said inner environment for measuring a particle concentration in the inner environment with said first measuring instrument of the particle measurement configuration.

13. The device according to claim 12, which comprises a vacuum-supplied handling device, wherein said feed connection is disposed on said handling device and is supplied from a further vacuum.

14. The device according to claim 12, wherein a probe having the feed connection is disposed on a handling device for handling objects selected from the group consisting of wafer-shaped objects, flat monitors, and masks for exposing semiconductor wafers.

15. The device according to claim 12, wherein a probe having the feed connection is disposed on a handling device for handling semiconductor wafers.

* * * * *